(12) United States Patent
Chen

(10) Patent No.: US 6,694,532 B2
(45) Date of Patent: Feb. 24, 2004

(54) ASSEMBLY SYSTEM FOR SECURING AN ADJUSTING STRAP TO A FRAME OF GOGGLES

(75) Inventor: Chih-Lung Chen, Tainan (TW)

(73) Assignee: High Rainbow Ent. Co., Ltd., Tainan (TW)

(*) Notice: Subject to any disclaimer, the term of this patent is extended or adjusted under 35 U.S.C. 154(b) by 0 days.

(21) Appl. No.: 10/178,489

(22) Filed: Jun. 25, 2002

(65) Prior Publication Data
US 2003/0233702 A1 Dec. 25, 2003

(51) Int. Cl.7 .................................................. A61F 9/02
(52) U.S. Cl. ................................................ 2/428; 2/452
(58) Field of Search ........................... 2/426, 428, 430, 2/431, 432, 436, 439, 440, 437, 443, 452; 24/170, 174, 186, 191, 196; 351/41, 43, 44, 62, 156, 157

(56) References Cited

U.S. PATENT DOCUMENTS

| 5,181,280 A | * | 1/1993 | Zachry, Jr. ............... 2/452 |
| 5,617,588 A | * | 4/1997 | Canavan et al. ............... 2/428 |
| 5,727,259 A | * | 3/1998 | Kawamata ............... 2/452 |
| 6,276,795 B1 | * | 8/2001 | Hall et al. ............... 351/62 |
| 6,349,421 B2 | * | 2/2002 | Fukasawa et al. ............... 2/428 |
| 6,350,030 B2 | * | 2/2002 | Fujima ............... 351/43 |

* cited by examiner

Primary Examiner—Gary L. Welch
(74) Attorney, Agent, or Firm—Rosenberg, Klein & Lee

(57) ABSTRACT

An assembly system for securing an adjusting strap to a frame of goggles includes a pair of goggles, two jointing blocks and an adjusting strap. The pair of goggles are provided with a cavity at each side of the frame. One side of each cavity has a groove, and a hollow is provided in each end of the lens. Each jointing block has a front inserting portion, a buckle ring and an operating member. A hooking foot is provided on the inward surface of each inserting portion, and each operating member has a flanged curve at the front end. A row of spaced teeth are provided on each end section of the adjusting strap, and each tooth has a slant surface on one side. The middle section of the adjusting strap has a plurality of flanged granules.

1 Claim, 6 Drawing Sheets

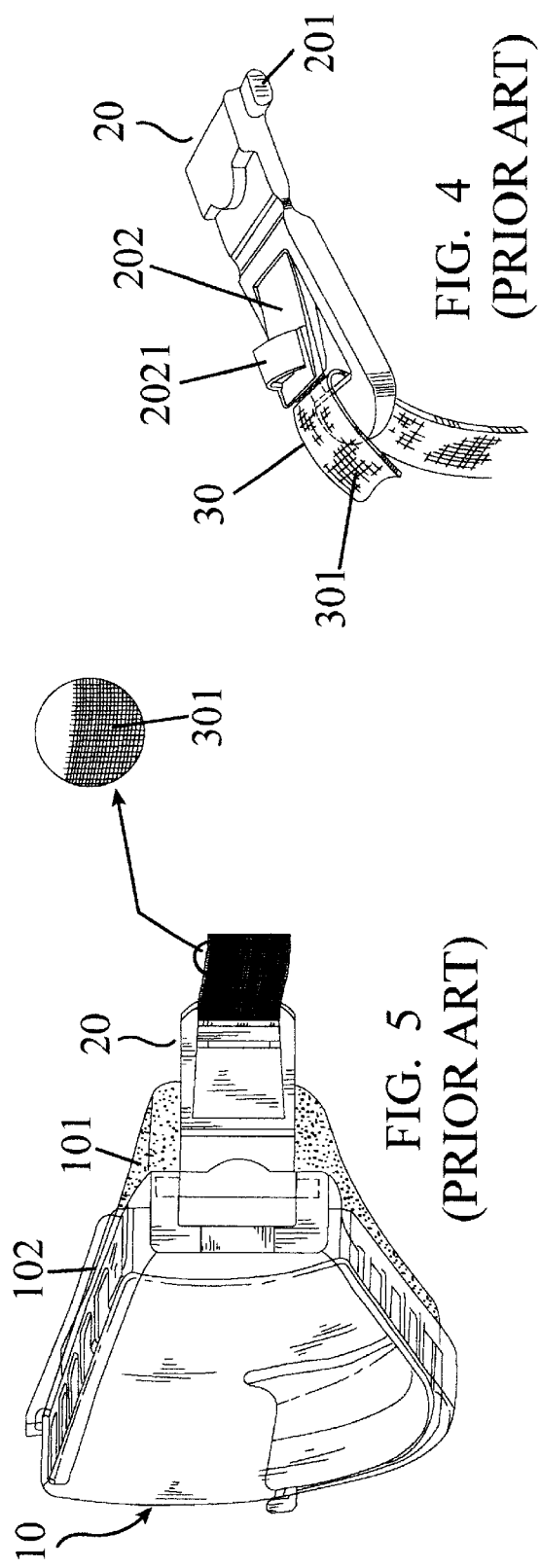
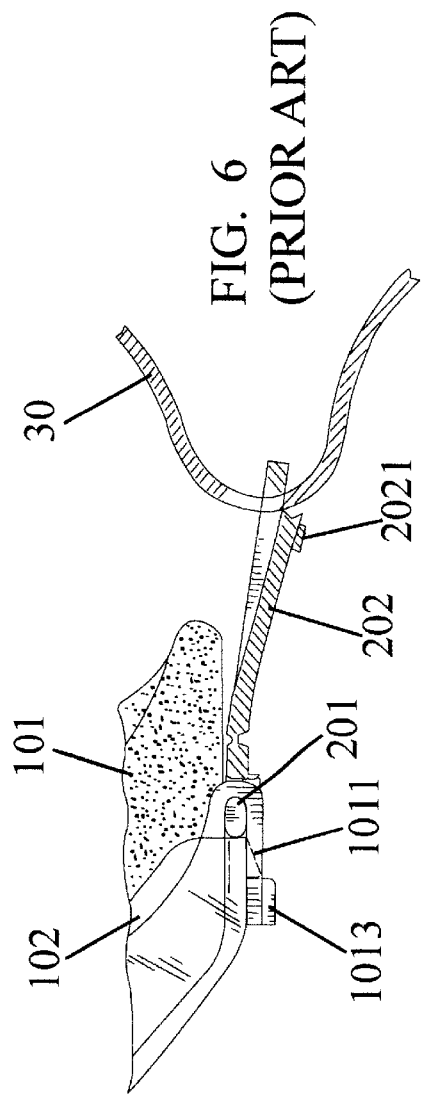
FIG. 4 (PRIOR ART)
FIG. 5 (PRIOR ART)
FIG. 6 (PRIOR ART)

ASSEMBLY SYSTEM FOR SECURING AN ADJUSTING STRAP TO A FRAME OF GOGGLES

BACKGROUND OF THE INVENTION

1. Field of the Invention

This invention relates to an assembly system for securing an adjusting strap to a frame of goggles with innovatory convenience and security features, and more particularly to an assembly system that can promptly and firmly assemble an adjusting strap to a frame of goggles.

2. Description of the Related Art

Many people whose eyes may be hurt by strong rays while working must wear industrial safety goggles to protect their eyes. Besides, many people who swim or work in the water must wear swim goggles to protect their eyes. Generally, a pair of conventional goggles is provided with an adjusting strap for a wearer to adjust the length to fit the wearer's head, so as to wear securely and comfortably.

Referring to FIGS. 1, 2 and 3, a pair of conventional goggles 10, is composed by an inner frame 101 and an outer frame 102. One jointing block 20 is provided to secure to each end of the goggles 10 and to be passed by an adjusting strap 30. Each jointing block 20 is provided with two protrusions 201 at both sides of the head portion, and the head portion of each jointing block 20 is inserted into each cavity 1012 in each protective ear 1011 of each inner frame 101, so as for the two protrusions 201 of each jointing block 20 to be caught in each cavity 1012 of each protective ear 1011. Each hook member 1021 of the outer frame 102 is inserted into each cavity 1012 to be against the catching piece 1013 of each protective ear 1011, so as to prevent the head portion of each jointing block 20 from falling off.

Referring to FIGS. 4, 5 and 6, the other portion of each jointing block 20 is a buckle ring with an operating strip 202, on each operating strip 202 is provided with a flange 2021, and a row of teeth are provided at the front end of each operating strip 202. When each operating strip 202 is moved outward by operating each flange 2021, each end of the adjusting strap 30 can pass through each buckle ring of each operating strip 202 and reach a predetermined position. When each flange 2021 of each operating strip 202 is released, the row of teeth of each operating strip 202 will grip the crisscross grains 301 in the adjusting strap 30, so as to make the adjusting strap 30 be secured to the frame of the goggles 10.

Although the conventional adjusting strap 30 can be secured to the frame of the goggles 10 by means of two jointing blocks 20, the parts are numerous, and the assembly process of each jointing block 20 to the goggles 10 is complicated, so as to add material and process cost. Moreover, because the crisscross grains 301 in the adjusting strap 30 are not deep enough and easily scraped away after a period of time, they can not be gripped firmly by the row of teeth of each operating strip 202, and the adjusting strap 30 will be easily moved when being slightly pulled.

SUMMARY OF THE INVENTION

Therefore, the present invention is to provide an assembly system for securing an adjusting strap to a frame of goggles that can substantially obviate the drawbacks of the conventional arts.

An objective of the present invention is to provide an an assembly system that can promptly and firmly assemble an adjusting strap to a frame of goggles.

Another objective of the present invention is to provide an assembly system which can save cost and time for assembly.

Yet another objective of the present invention is to provide an assembly system whose each jointing block has an operating member being provided with a flange convenient for being operated by a user.

It is a further objective of the present invention is to provide an assembly system whose adjusting strap will not be scraped away after being used for a long time.

Accordingly, an assembly system for securing an adjusting strap to a frame of goggles includes a pair of goggles, two jointing blocks and an adjusting strap. The pair of goggles are provided with a cavity at each side of the frame for a jointing block. One side of each cavity has a groove, and a hollow is provided in each end of the lens. Two jointing blocks are respectively connected with one end of the frame. Each jointing block has a front inserting portion, and a hooking foot is provided on the inward surface of each inserting portion so as to be caught in each hollow of the lens, and the other portion of each jointing block is formed as a buckle ring. An upper operating member extends above each buckle ring, and each operating member has a flanged curve at the front end. Both end sections of the adjusting strap are provided to respectively pass each buckle ring, a row of spaced teeth are provided on each end section, and each tooth has a slant surface on one side. The middle section of the adjusting strap is provided with a plurality of flanged granules.

BRIEF DESCRIPTION OF THE DRAWINGS

Other features and advantages of the present invention will become apparent in the following detailed description of the preferred embodiments with reference to the accompanying drawings, in which:

FIG. 4 is a perspective view of the conventional jointing block being assembled with an adjusting strap;

FIG. 5 is a side elevation view of the conventional goggles, a jointing block and an adjusting strap in an assembled configuration;

FIG. 6 is a top sectional view of the conventional goggles, a jointing block and an adjusting strap in an assembled configuration;

DETAILED DESCRIPTION OF THE
PREFERRED EMBODIMENTS

Figure 1:
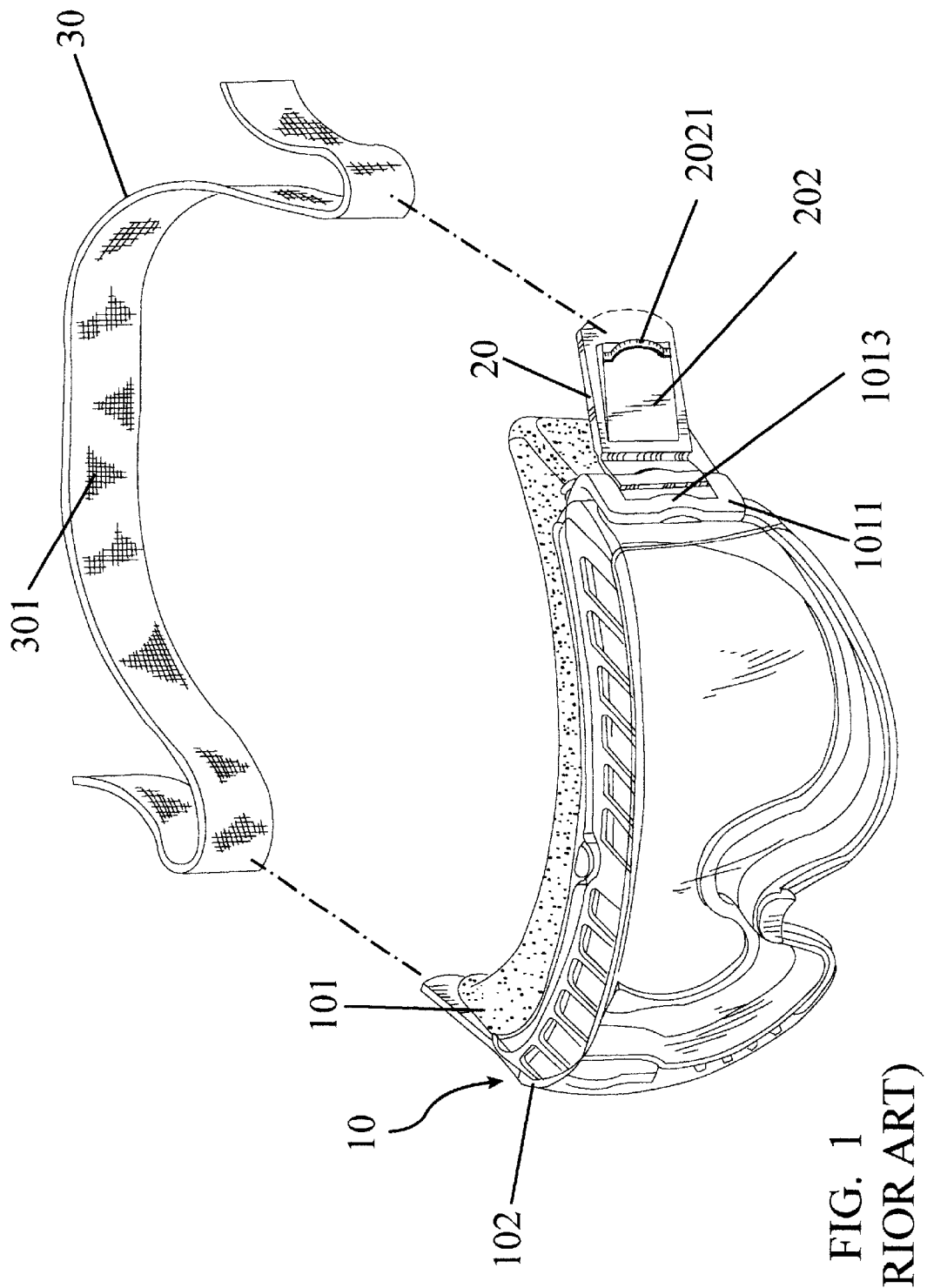
FIG. 1 is an exploded perspective view of a conventional goggles, jointing blocks and an adjusting strap.
Figure 2:
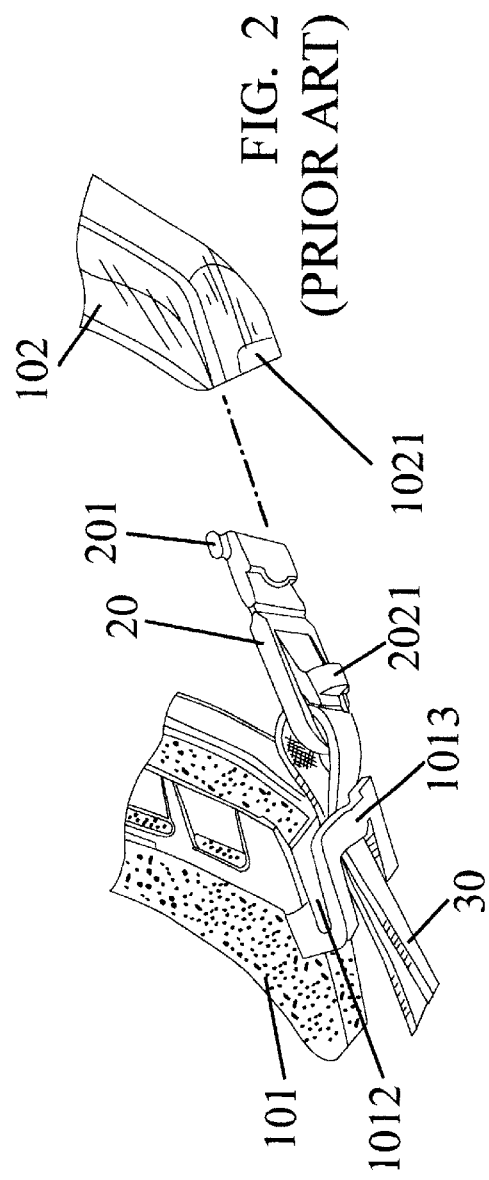
FIG. 2 is an exploded perspective view of the inner frame, outer frame of the conventional goggles, the jointing block and an adjusting strap.
Figure 3:
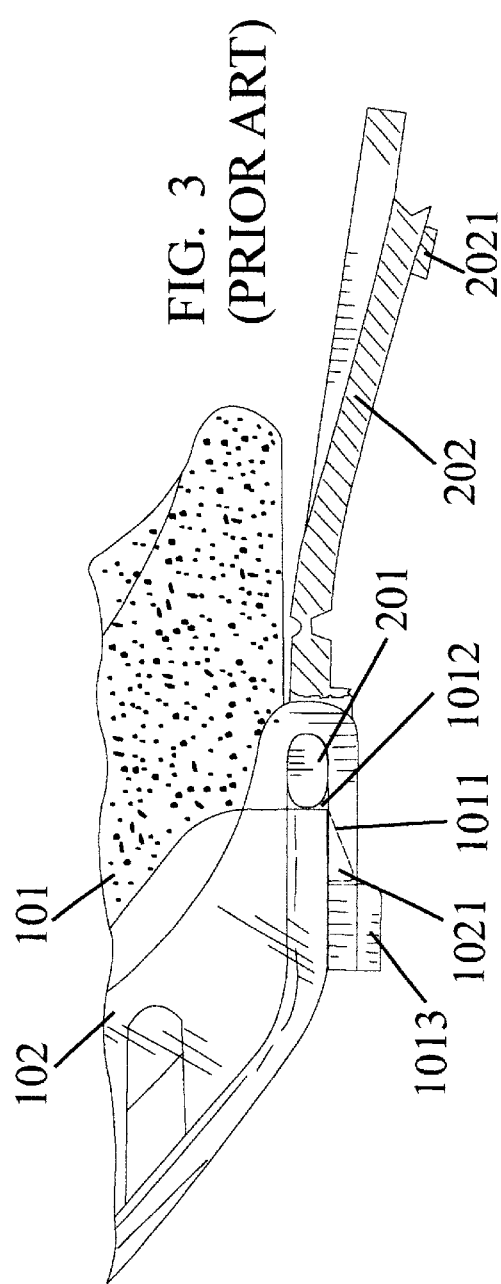
FIG. 3 is a top elevation view of the conventional goggles and a jointing block in an assembled configuration.
Figure 7:
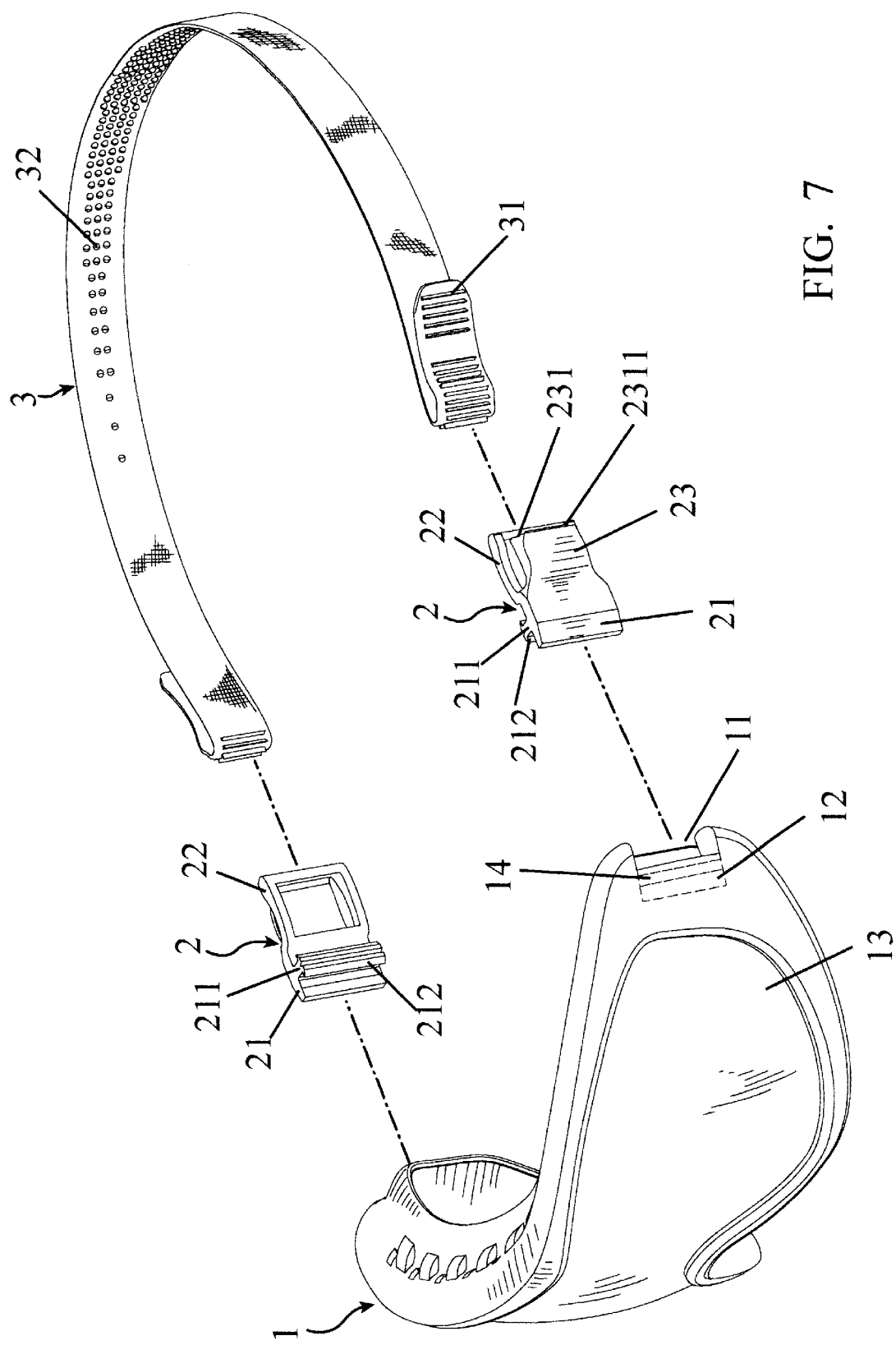
FIG. 7 is an exploded perspective view of an embodiment of a pair of goggles, two jointing blocks and an adjusting strap in accordance with the present invention.

Referring to FIG. 7, an assembly system for securing an adjusting strap 3 to a frame of goggles 1 includes a pair of goggles 1, two jointing blocks 2 and an adjusting strap 3. The pair of goggles 1 are provided with a cavity 11 respectively at each side of the frame for receiving a jointing block 2. One side of each cavity 11 has a groove 12, and a hollow 14 is provided in each end of the lens 13.

Two jointing blocks 2 are respectively connected with one end of the frame of the goggles 1. Each jointing block 2 has a front inserting portion 21, and a hooking foot 211 is provided on the inward surface of each inserting portion 21. Two barbs 212 are provided at the bottom end of each hooking foot 211 so as to be caught in each hollow 14 of the lens 13, and the other portion of each jointing block 2 is formed as a buckle ring 22. An upper operating member 23 extends above each buckle ring 22, each operating member 23 has a curve 231 at the front end, and at the top end of each curve 231 is provided with a flange 2311 convenient for operation. Both end sections of the adjusting strap 3 are provided to respectively pass each buckle ring 22, a row of spaced teeth 31 are provided on each end section, and each tooth 31 has a slant surface 311 on one side. The middle section of the adjusting strap 3 is provided with a plurality of flanged granules 32 to add friction with the hair of a wearer.

Figure 9:
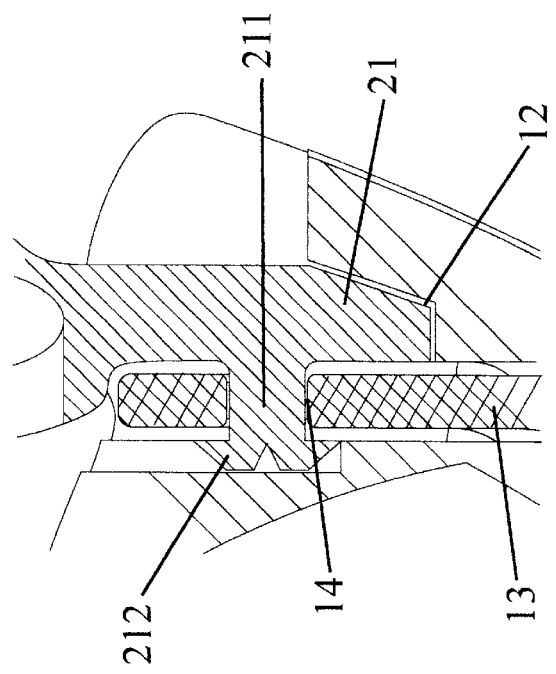
FIG. 9 is an enlarged cross sectional view taken from the circle in FIG. 8.
Figure 8:
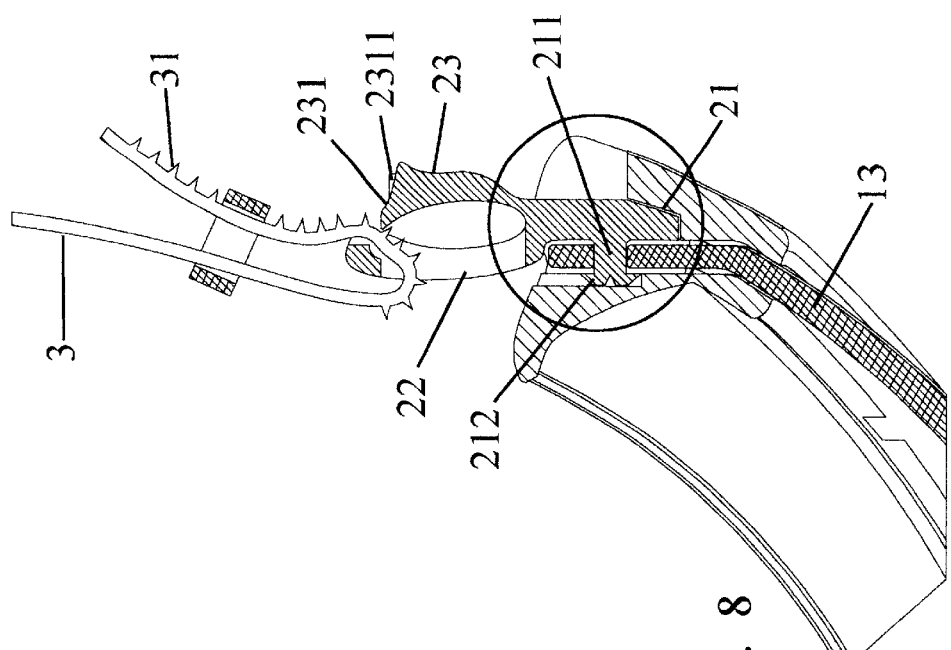
FIG. 8 is a cross sectional view of an embodiment of a pair of goggles, a jointing block and an adjusting strap in an assembled configuration in accordance with the present invention.

While the assembly system in the present invention is assembled, referring to FIGS. 8 and 9, the front inserting portion 21 of each jointing block 2 is inserted into the groove 12 of each cavity 11 in the goggles 1, and the hooking foot 211 on the inward surface of each inserting portion 21 is inlaid in the hollow 14 of each end of the lens 13, so as for the two barbs 212 at the bottom end of each hooking foot 211 to be firmly caught in each hollow 14.

Figure 10:
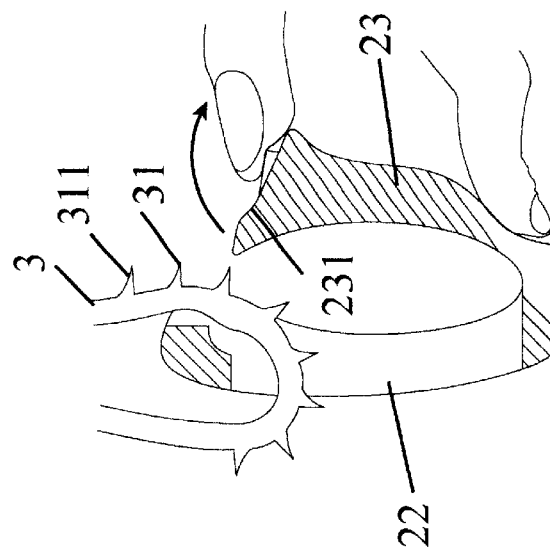
FIG. 10 is a top elevation view of an embodiment of the jointing block being assembled with the adjusting strap in accordance with the present invention.
Figure 11:
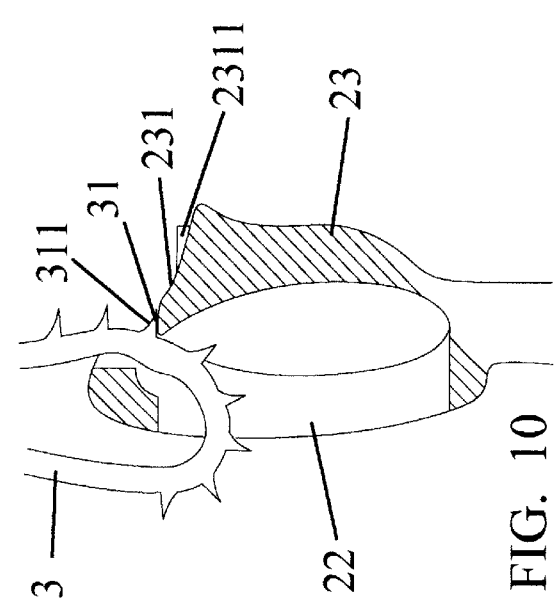
FIG. 11 is a schematic top elevation view of showing the flanged curve of the jointing block being operated to separate from one tooth on the adjusting strap in accordance with the present invention; and, FIG. 12 is a side elevation view of an embodiment of a pair of goggles, a jointing block and an adjusting strap in an assembled configuration in accordance with the present invention.
Figure 12:
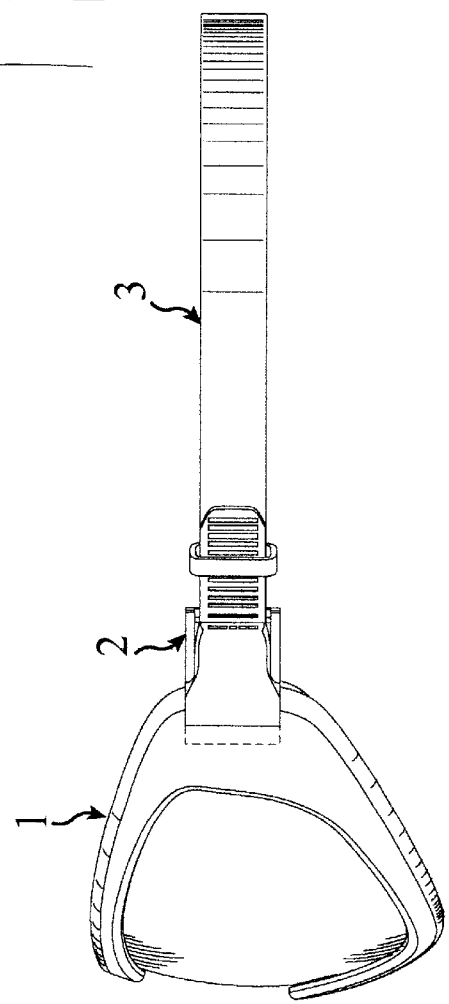

Referring to FIGS. 10,11 and 12, each operating member 23 above each buckle ring 22 is moved outward by operating the flange 2311 on the curve 231 at the front end, 15 and each end of the adjusting strap 3 passes through each buckle ring 22 and reaches a predetermined position. When each operating member 23 is released, the bottom end of each curve 231 will be against one tooth 31, so as to prevent the adjusting strap 3 from moving and to make the adjusting 20 strap 3 be firmly secured to the frame of the goggles 1. Each end of the adjusting strap 3 is inserted in a securing ring to finish the assembly.

While the preferred embodiments of the invention have been described above, it will be recognized and understood that various modifications may be made therein, and the appended claims are intended to cover all such modifications which may fall within the spirit and scope of the invention.

What is claimed is:

1. An assembly system for securing an adjusting strap to a frame of goggles comprising:

a pair of goggles being composed by a frame and a lens, a cavity being provided at each side of said frame for receiving a jointing block, one side of each said cavity having a groove, a hollow being provided in each end of said lens;

an adjusting strap being provided with a row of spaced teeth on each end section, each said tooth having a slant surface on one side, a middle section of said adjusting strap being provided with a plurality of flanged granules to add friction; and, two jointing blocks being provided to respectively connect with one end of said frame of said goggles, each said jointing block having a front inserting portion, a hooking foot being provided on an inward surface of each said inserting portion, two barbs being provided at the bottom end of each said hooking foot, so as to be caught in a respective one of said hollows of said lens, an opposing portion of each said jointing block being formed as a buckle ring for a respective end section of said adjusting strap to be passed thereby and having an operating member extending above said buckle ring, said operating member having a a portion of a distal end thereof adapted for engaging a respective one of said teeth of said adjusting strap, said distal end of said operating member having a flange formed thereon for use by a user in displacing said operating member to disengage said portion of said distal end from said respective one of said teeth and thereby release said end section of said adjusting strap from said jointing block.

* * * * *